United States Patent [19]

Kittscher et al.

[11] Patent Number: 4,475,663

[45] Date of Patent: Oct. 9, 1984

[54] PROCESSES AND MEANS FOR PERFUMING PACKAGING CONTAINERS

[75] Inventors: Peter Kittscher, Kaarst; Klaus Schumann, Erkrath; Theodor Altenschöpfer, Düsseldorf; Wolfgang Haumann, Hilden, all of Fed. Rep. of Germany; Heinz G. Smolka, Randburg, South Africa

[73] Assignee: Henkel Kommanditgesellschaft auf Aktien, Düesseldorf, Fed. Rep. of Germany

[21] Appl. No.: 462,467

[22] Filed: Jan. 31, 1983

[30] Foreign Application Priority Data

Jul. 22, 1982 [DE] Fed. Rep. of Germany ....... 3227370

[51] Int. Cl.[3] ...................... B65D 51/30; B65D 81/28; A61L 3/00

[52] U.S. Cl. ...................................... 220/87; 206/205

[58] Field of Search ........................ 206/210, 205, 0.5; 220/87, 454

[56] References Cited

U.S. PATENT DOCUMENTS

| | | | |
|---|---|---|---|
| 920,711 | 5/1909 | Allen | 220/87 |
| 1,836,297 | 12/1931 | Vienna | 220/87 |
| 2,314,146 | 3/1943 | Katz | 206/205 |
| 2,798,636 | 7/1957 | Ketchledge | 220/87 |
| 3,441,353 | 4/1969 | Claff | 206/0.5 |
| 3,771,254 | 11/1973 | Scott et al. | 220/454 |
| 3,955,706 | 5/1976 | Whitaker | 220/87 |
| 4,105,144 | 8/1978 | Lin | 206/205 |
| 4,202,472 | 5/1980 | Lin | 206/205 |
| 4,349,104 | 9/1982 | Hayes | 206/205 |

FOREIGN PATENT DOCUMENTS

| | | |
|---|---|---|
| 4463 | 10/1979 | European Pat. Off. . |
| 32019416 | 1/1982 | Fed. Rep. of Germany . |

*Primary Examiner*—William T. Dixson, Jr.
*Attorney, Agent, or Firm*—Ernest G. Szoke; Henry E. Millson, Jr.; Mark A. Greenfield

[57] ABSTRACT

Processes and means for perfuming packaging containers wherein absorbable carrier materials, preferably in the form of a disc, are separately perfumed and then attached to an inner wall of the packaging container.

8 Claims, 1 Drawing Figure

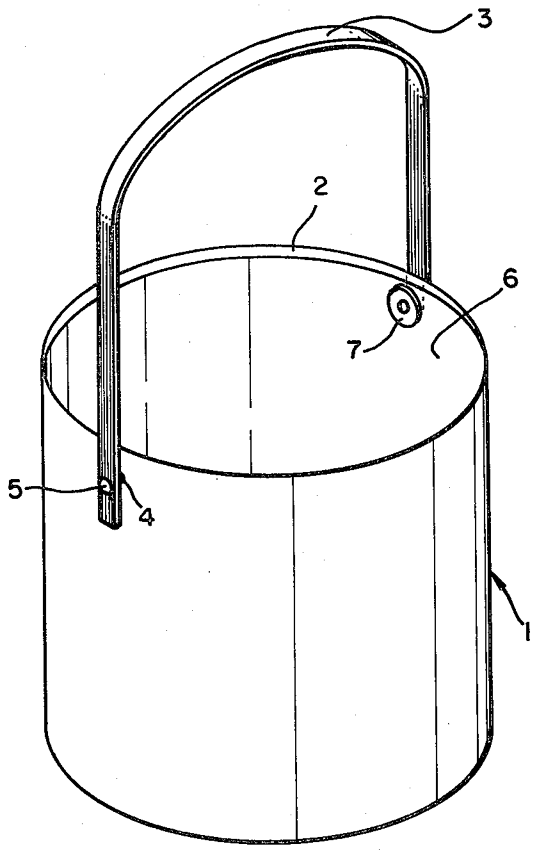
3
2
6
7
5
4
1

PROCESSES AND MEANS FOR PERFUMING PACKAGING CONTAINERS

BACKGROUND OF THE INVENTION

This invention relates to a process and means for perfuming packaging containers.

Detergent and cleaning materials are usually offered in perfumed form. The perfumes are usually contained within the product so that the consumer is exposed to the perfume when he opens the package as well as during use of the product.

However, perfumes are unstable to a number of constituents contained in detergent and cleaning materials. This is true, for example, with respect to chlorine in hypochlorite or chlorine bound to organic chlorine carriers such as sodium dichloroisocyanurate and trichloroisocyanuric acid. Also perborates in combination with bleach activators can negatively influence the stability of the perfumes. These disadvantages can be alleviated in accordance with European patent application No. 4,463 by perfuming the shipping materials, in particular, the cartons used for packaging. Direct contact of the perfumes with the interfering contents will then not take place. Preferably, the perfumes are applied to the inner upper portion of the package in order to impregnate the carton materials.

In practice it was found that a number of carton materials only slowly absorb the perfumes when the perfume is applied dropwise or by spraying. The perfumes will leave behind a "nose-shaped form" and visible spots. In addition, when spraying the perfumes, the misting that occurs when this is carried out not only causes waste, but causes odor irritation in the surrounding area. In prior German patent application No. 32 01 941.6, a process was disclosed to perfume the packaging materials, wherein the perfume was made into a high viscosity paste prior to application and was then applied in the form of the paste to the packaging materials. In this instance, the direct perfuming of the product is avoided and, thereby, the amount of perfume needed is reduced. In addition, when using the perfume in the form of a paste, reduced odor invasion of the work place, as well as reduced losses of perfume result.

However, a common disadvantage of all of the above procedures to perfume packaging materials is the fact that larger barrels, such as round containers, cartons, round and rectangular drums, etc., which are increasingly used as packaging containers, can only be perfumed with the desired product shortly before the containers are filled. Long storage periods after perfuming, as well as perfuming in advance become barely possible or even impossible because eventually contamination of the surrounding area with the perfume as well as loss of the perfume would be too great. Until now, such disadvantages could only be avoided when the barrels were closed and sealed with foil or stored in a cool area. However, such processes are very uneconomical.

BRIEF DESCRIPTION OF THE DRAWING

The drawing gives a perspective view of a container showing the preferred positioning of the perfumed carrier material of the invention in disc form.

DESCRIPTION OF THE INVENTION

This invention relates to a process and means for perfuming containers, wherein perfuming is possible in advance without large losses of perfume or contamination of the environment, and cooling is unnecessary. The process in accordance with the invention consists of first perfuming an absorbable carrier material, which step is carried out separately, and then attaching it to the inside of the container.

In accordance with the invention, the packaging containers are perfumed by the use of absorbable carrier components, preferably in the form of discs, which have only indirect contact with the container. Preferred are absorbable discs made of cardboard or pasteboard, laminated on one side with metal or synthetic foil. The foil surface faces the container wall and the cardboard or pasteboard side faces the inside of the container. The absorbable pasteboard or cardboard material of the disc-shaped carrier should have a Cobb-30 value of more than 100 $g/m^2$.

The perfumed carrier materials, preferably in disc form, are applied by gluing or riveting to the container, preferably to the upper section of the container on the inside wall thereof. It is advantageous to apply this carrier material in such a manner that direct contact with the product in the container is avoided. The attachment is preferably carried out through riveting to the container, such as to a drum or a rectangular container, or onto the handles or the carrying straps thereof. Thereby the carrier material, particularly when in the form of pasteboard or cardboard discs, also acts as a reinforcing function, like a gasket in a riveted area. This makes it possible, for example, to reduce the weight per area for the carton material used for the package, which is usually about 700 to 800 $g/m^2$, by 50 $g/m^2$.

Another advantage of the individually perfumed carrier materials of the invention is that they become an indirect part of the packaging itself, so that when manufacturing the individual containers, materials can be used which otherwise could not be used due to their very low absorptive properties for perfume oils. Packaging materials that have inside barrier layers, for example, those made of synthetic materials, metal foil, or barrier paints can be readily used with the individually perfumed carriers of the invention.

The main advantages of the process of the invention are in the area of logistics. The perfuming can be achieved away from the production area and the packaging area; namely, in a separated, centrally located area where the perfume selected for the carrier material can be applied. Due to the small volume of the perfumed carrier, the selected discs or other shapes can be riveted without problems, and can be sealed inside foil and/or in enclosed containers. Perfume losses worth mentioning or which cause a problem will not occur, even if no cooling is carried out. The use of the perfumed carrier materials is preferably carried out during packaging shortly before the individual containers are filled. Preferably, the carrier material is shaped to the desired shape and size prior to perfuming, although it is of course also possible to perfume a larger quantity of the carrier material and then cut it to the desired shape or shapes thereafter, and such variation, while usually less economical, is also within the scope of the invention.

The absorbable carrier materials are preferably treated with the perfume by spraying, by drops, or by wiping with a pure form of the perfume, or with a paste of the perfume which is to be used containing perfume adjuvant materials. When temporarily storing the perfumed carrier materials, up to periods of several weeks, the perfume applied to the absorbable carrier material will be evenly distributed without much of a problem.

Details of the invention are set forth in the schematic drawing, which shows a working example of the invention. This example is given for illustration purposes only and not to limit the invention.

EXAMPLE

In the drawing, the top area of a drum 1 used to hold detergents is shown in a perspective view. Handle 3 is riveted to drum 1 below stabilizing rim band 2. Rivet 4 has a relatively large head 5 on the outside of handle 3, and is fixed to inside wall 6 of drum 1 with the perfumed disc 7 of the invention, which also assumes the function of a gasket.

The gasket which is needed at the end of rivet 5 to stabilize or properly seat the rivet into the wall of the drum, is also the disc used as the carrier material for perfuming, so that no additional gaskets or other positioning devices are required in the practice of the invention. The fastening of this disc can wait until immediately prior to the time that drum is is to be filled with the desired product. Since handle 3 is attached to the upper area of the drum, there is practically no danger that contact will occur between the perfumed carrier material and the product contained in the drum.

What is claimed is:

1. A process for perfuming a packaging container comprising the steps of:

(a) applying a perfume to a disc shaped absorbable carrier material at a location remove from said packaging container, wherein the disc shaped absorbable carrier material contains a substantially air impermeable layer on one side thereof; and (b) attaching all or a portion of the resulting perfumed disc shaped carrier material to an inside wall of the packaging container at a location thereon where the contents of the packaging container will not normally come into contact therewith, wherein the perfumed disc shaped carrier material is positioned on said inside wall so that the air impermeable layer faces said inside wall, and wherein the perfumed disc shaped carrier material is also attached to a handle or strap on the outside wall of the packaging container by means of a rivet.

2. A process in accordance with claim 1 wherein the perfume is applied to the absorbable carrier material in pure form or as a paste with perfume adjuvants.

3. A process in accordance with claim 1 wherein a period of up to several weeks elapses between step (a) and step (b).

4. A process in accordance with claim 1 wherein step (b) is carried out shortly before the packaging container is filled and closed.

5. A process in accordance with claim 6 wherein step (b) is carried out shortly before the packaging container is filled and closed.

6. A process in accordance with claim 1 wherein the absorbable carrier material is cardboard or pasteboard.

7. A perfumed absorbable carrier material in the form of a disc for attachment to an inside wall of a packaging container, wherein said disc contains a substantially air impermeable layer on one side thereof which is composed of metal or a synthetic foil, and wherein said disc is also adapted to act as a gasket on the inside wall of a packaging container for attachment with a rivet through the wall of the packaging container to a handle or strap.

8. A perfumed absorbable carrier material in accordance with claim 7 wherein said material is cardboard or pasteboard.

* * * * *